US00PP07871P

United States Patent [19]

Holtkamp, Sr.

[11] Patent Number: Plant 7,871

[45] Date of Patent: May 19, 1992

[54] AFRICAN VIOLET PLANT NAMED MARIA ANTONIA

[76] Inventor: Reinhold Holtkamp, Sr.,
Blumenstrasse 28, D 4242
Rees-Haffen, Fed. Rep. of Germany

[21] Appl. No.: 551,445

[22] Filed: Jul. 12, 1990

[51] Int. Cl.[5] ..... A01H 5/00
[52] U.S. Cl. ..... Plt./69
[58] Field of Search ..... Plt./69

[56] References Cited

U.S. PATENT DOCUMENTS

P.P. 3,206 6/1972 Holtkamp ..... Plt. 69

P.P. 5,595 12/1985 Yoshida ..... Plt. 69

*Primary Examiner*—James R. Feyrer
*Attorney, Agent, or Firm*—Foley & Lardner

[57] ABSTRACT

A new and distinct cultivar of African violet named Maria Antonia characterized by its single violet-shaped, pearl-color flowers with frilled edges; strong, upright flower stems that curve slightly toward the center to form a bouquet above the leaves; dark green, oval to heart-shaped leaves; profuse flowering, vigorous and compact growth habit, flowering 10–11 weeks after potting, and its long lasting and non-dropping flowers.

1 Drawing Sheet

The present invention comprises a new and distinct cultivar of African violet plant, botanically known as *Saintpaulia ionantha*, and hereinafter referred to by the cultivar name Maria Antonia.

The new cultivar was referred to during the breeding and selection process by the designation 826/2 and is a product of a planned breeding program. The new cultivar was originated from a cross made by me in the controlled breeding program in Haffen, Federal Republic of Germany. The female, or seed parent was a cultivar designated 2850. The male, or pollen parent was a cultivar designated 1970.

Maria Antonia was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Maria Antonia has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Maria Antonia, which in combination distinguish this African violet as a new and distinct cultivar:

(1) Strong, upright flower stems curving slightly toward the center.

(2) Pearl-color, single flowers with frilled edges.

(3) Profuse flowering.

(4) Each plant carries 10–13 and more upright flower stems each of which carries 8–10 and more flowers.

(5) Long lasting, non-dropping flowers.

(6) Vigorous and compact grower.

(7) Plant saleable 10 to 11 weeks after potting.

(8) Seed capsules push slightly through.

(9) Dark green, oval to heart-shaped leaves.

(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 a.m. in Nashville, Tenn.

Botanical Classification: *Saintpaulia ionantha*, Ramat., c.v. Maria Antonia.

Parentage:

*Male parent.*—1970.

*Female parent.*—2850.

Propagation: The new cultivar holds its distinguishing characteristics through successive propagations by leaf cuttings.

Plant. From 9 cm to 12 cm tall when grown in pots, and approximately 24–28 cm in diameter when fully grown.

Leaves:

*General form.* Oval to heart-shaped.

*Diameter.*—64–75 mm wide and 70–80 mm long.

*Texture.*—Leatherlike.

*Aspect.*—Shiny, hairy, slightly serrated.

*Veins.*—Upperside; visible; underside: well pronounced, light green or purplish green, shiny.

*Color (upperside).*—Yellow-Green Group 147 A and darker.

*Color (underside).*—Greyed-Purple Group 186 A.

*Pedtiole.*—Strong upright, purplish brown, hairy.

Flower:

*Buds.*—Bell-shaped, 5–7 mm just before opening, light green.

*Sepals.*—Five (5). Color: Purplish brown.

*Calyx.*—Shape: Funnel-shaped. Aspect: Spear-shaped, hairy.

*Peduncle.*—Character: Strong upright, hairy. Color: Purplish brown.

Individual flowers:

*Size.*—35–40 mm.

*Shape.*—Single, violet-shaped with frilled edges.

*Color (upperside).*—Red Group 56 D and lighter, edges sometimes 56 D to C. Under cooler temperatures and more intensive lighting, the color tends to intensify.

*Color (underside).*—Red Group 56 D and lighter.

*Borne.*—Each flower stem carres 8–10 and more flowers on strong, upright peduncle that are free standing above the leaves, thereby forming a bouquet.

*Flowering habit.*—Flowers 10–11 weeks after potting.

Reproductive organs:

*Stamens.* Two (2).

*Anthers.*—2 composed of 4 anther cells, seed capsules push slightly through.

*Filaments.*—Yellowish, 3–4 mm long.

Pollen color.—Yellow Group 7 A.

Styles.—7–8 mm long, very light pink, base of ovary light green and hairy.

Roots: Normally developed, white when young, turning slightly brownish when older.

Disease resistance. Good.

General observations: Maria Antonia has an extremely attractive due to its sparkling, pearl-color flowers with frilled edges. A nice bouquet of flowers free standing above the leaves develops after approximately 10–11 weeks. Each of the 10–13 and more strong flower stems carries 8–10 and more single violet-shaped flowers which are long-lasting and non-dropping. Occasionally, one to two additional small petals may develop in the center. The bouquet is surrounded by dark green, oval to heart-shaped leaves. The seed capsules push slightly through.

I claim:

1. A new and distinct cultivar of African violet named Maria Antonia, as described and illustrated, and particularly characterized by its single violet-shaped, pearl-color flowers with frill ededges; strong, upright flower stems that curve slightly toward the center to form a bouquet above the leaves; dark green, oval to heart-shaped leaves; profuse flowering, vigorous and compact growth habit, flowering 10–11 weeks after potting, and its long lasting and non-dropping flowers.

* * * * *

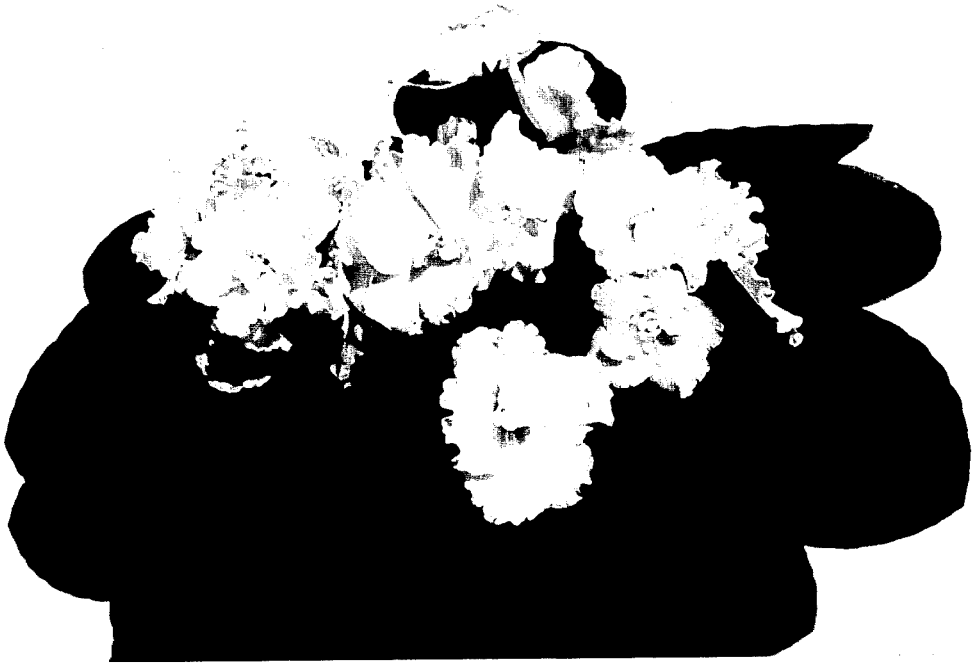
/